United States Patent [19]

Rosenberger

[11] Patent Number: 5,174,313
[45] Date of Patent: Dec. 29, 1992

[54] GERMICIDAL DENTAL FLOSS AND METHOD FOR FABRICATION

[76] Inventor: Edwin D. Rosenberger, 328 E. 5th St., Apt. 1, Brooklyn, N.Y. 11218

[21] Appl. No.: 741,585

[22] Filed: Aug. 7, 1991

Related U.S. Application Data

[63] Continuation-in-part of Ser. No. 459,181, Dec. 29, 1989, Pat. No. 5,040,554, which is a continuation-in-part of Ser. No. 243,621, Sep. 13, 1988, abandoned.

[51] Int. Cl.⁵ .............................................. A61C 15/00
[52] U.S. Cl. ................................................... 132/321
[58] Field of Search ................... 132/321, 323; 427/2, 427/203; 514/900, 902; 424/435

[56] References Cited

U.S. PATENT DOCUMENTS

| | | | |
|---|---|---|---|
| 3,897,795 | 8/1975 | Engel | 132/321 |
| 4,029,113 | 6/1977 | Guyton | 132/321 |
| 4,291,017 | 9/1981 | Beierle et al. | 433/216 |
| 4,446,140 | 5/1984 | Nelson | 514/289 |
| 5,040,554 | 8/1991 | Rosenberger | 132/321 |

*Primary Examiner*—Cary E. O'Connor
*Attorney, Agent, or Firm*—Richard L. Miller

[57] ABSTRACT

A germicidal dental floss having a coating of the active material typically a phenol derivative/compound removably fixed thereon by a binder such as wax. The active material is rubbed off by contact with the teeth thereby treating areas between the teeth and gums for improved oral hygiene.

13 Claims, No Drawings

GERMICIDAL DENTAL FLOSS AND METHOD FOR FABRICATION

The present Application is a Continuation-In-Part application of Ser. No. 07/459,181, filed on Dec. 29, 1989, now U.S. Pat. No. 5,040,554, which is a further Continuation-In-Part of application of Ser. No. 07/243,621, filed on Sep. 13, 1988, which has been abandoned, but for which there has been maintained a continuous chain of copendency.

BACKGROUND OF THE INVENTION

This invention relates generally to an improved dental floss of the antibacterial/analgesic type, and, more specifically to a germicidal dental floss and a process for making same.

The art to which this invention relates of which applicant is already aware, includes the following U.S. Pat. Nos. 719,017; 3,830,247, 3,342,539.

The first of these describe the combination with a toothpick of a holder having a discharging duct, a handle having a reservoir of antiseptic liquid, a reciprocating plunger for expelling liquid through the duct and onto the toothpick for discharging antiseptic between and at the roots of teeth while also picking the teeth. U.S. Pat. No. 3,830,247 discloses dental floss impregnated with antiseptic in a housing therefore wherein the floss passes through a reservoir of antiseptic. U.S. Pat. No. 3,342,539 teaches a dental floss which comprises a length of conventional construction terminating in a porous section which when pre-soaked prior to use, in an antiseptic solution, then delivered into interdental spaces as the floss is used normally to physically remove food particles from between the teeth.

Applicant is also aware of U.S. Pat. Nos. 2,667,443; 3,838,702; 3,897,795; and 4,029,113.

U.S. Pat. No. 2,667,443 teaches the impregnation of dental floss both by dry, waxborn and resin bound carriers with therapeutic, cleaning agents or medicaments.

U.S. Pat. No. 3,838,702 teaches a dental floss having an improved cleaning and polishing action obtained by coating the floss with a coating agent comprising a resilient wax, polymer or elastomer, having embedded therein a finely divided, particulate, polishing agent. In addition, the incorporation of various adjuvant materials into the coating agent such as coloring matter, flavoring, medicinals or therapeutic agents is suggested.

U.S. Pat. No. 3,897,795 teaches that binding or coating floss fibers with wax is unsuitable where bacterially active matter is to be incorporated in the floss, as wax coating resisted or repelled water and provided an indifferent binder for solids, directing instead the use of a soap or detergent binder in which bacterially active matter can be simultaneously bonded or impregnated in the floss fibers. The application may take place through using squeegees and/or squeegee rollers, by using a volatile ingredient as a solvent for the active agent and/or binder or by pulling the floss through a paste mix of the active agent.

U.S. Pat. No. 4,029,113 teaches a waxed dental textile material having a fluorine compound distributed through the wax coating which provides fluoride iron in a therapeutic amount to inhibit the formation of dental cavities.

As will be seen hereinafter, none of these disclose applicant's novel, unique and unobvious product and process which overcomes the prejudice of the prior art against using a wax binder or coating for floss where bacterially active matter is incorporated in the floss.

SUMMARY OF THE INVENTION

In its product aspect, this invention resides in a dental floss coated with a microcrystalline wax containing a prophylactic, antimicrobial analgesic and/or antiseptic material.

More particularly, the invention concerns a prophylactic dental floss comprising a flexible length of floss having at least on the exterior thereof a coating of a phenol derivative/compound germicidal material typically selected from the group of synonyms generally known and consisting of 4-hexylresorcinol; or 1,3-benzenediol,-4-hexyl or alternatively sodium phenolate and a binder removably securing said material to said length of floss. The coating may include from 0.001 to 25 percent by weight of said germicidal material, the remainder of the coating being said binder.

When a high degree of sepsis is present a coating from 25 to 75 percent by weight of germicidal material, may be more beneficial.

In a particularly advantageous form, the coating includes 4-hexylresorcinol in an analgesic combination, preferably 25 to 75 percent by weight of the mixture combining a powerful germicidal and analgesic action.

In its process aspect, the invention includes mixing at least one of the above listed materials with a wetting liquid comprising a low melting point binder or solvent, coating a dental floss therewith, and allowing said coating to cool and solidify or to dry.

DESCRIPTION OF BEST MODE OF THE INVENTION

The floss used herein can be made of conventional floss material such as flexible plastic, nylon, polyethylene, polypropylene and the like. Accordingly there is no need to illustrate same. The active/prophylactic material is a phenol derivative/compound germicidal material typically selected from the group of synonyms generally known and consisting of 4-hexylresorcinol; or 1,3-benzenediol,-4-hexyl or alternatively sodium phenolate.

The binder for fixing the above material onto the floss is a non-toxic, sterile, low melting material such as microcrystalline wax; preferably one that softens at mouth temperature. In the process of making the floss, the binder is melted and the active/prophylactic material is dissolved therein in a suitable receptacle. The thread or floss is dispensed from a spool thereof and passed through the hot coating mixture. The coated thread is allowed to cool. Thereby forming at least an external coating on the floss. The amount of active material in the coating can be varied according to desired end use. Thus, to make a floss intended for use in a regular maintenance program, the coating mixture can contain from 0.001 to 25 percent by weight of active material, the remainder (75%) being binder. For use as needed in the control of minor infections in the gum tissues, the concentration of the coating will range from 25 to 75 percent by weight, the remainder being binder with the exact amount also dependent on the binder's properties, and, in particular, the solubility of the active material therein.

In operative use, the floss of the invention is inserted into the crevices or spaces between the mouth teeth and then is pulled therethrough. Thus, the active material is wiped off the floss and onto the dental crevice surfaces and gums thereby treating the same and inhibiting germ growth there and the like. Suitably, the floss may be coated in a device of the type shown in U.S. Pat. No. 3,830,247.

The invention contemplates the following alternative methods of applying the active ingredient to the floss.

Another method of waxing is by preparing a solution of wax in a volatile solvent subsequently evaporated out.

The wax may alternatively be applied as a aqueous emulsion.

As an alternative to bathing the unwaxed floss in a bath of liquid wax, the wax may be applied by metering rolls with a felt applicator supplied with liquid wax thereby to saturate the unwaxed floss passed therebetween.

Where it is desired to avoid waxed floss, a soap or detergent may instead be used as a binder for the prophylactic material and applied to the floss.

Alternatively, the floss may be impregnated with a mixture of a dry germicidal powder which has been diluted with a dry inert powder and subsequently coated with a water-soluble cellulose derivative such as methyl cellulose or sodium carboxymethyl cellulose as a binder.

As a further alternative, a water-soluble binder can be mixed with water and the active/prophylactic (germicidal) ingredient. The floss is then coated with such mixture.

Without further analysis, the foregoing will so fully reveal the gist of this invention that those skilled in the art can by applying current knowledge thereto readily adapt if for various applications without omitting certain features which can constitute essential characteristics of the generic or specific aspects of this invention. Therefore, a more lengthy description is deemed unnecessary.

It is intended that various changes may be made in this invention in the practical development thereof, if desired. Such changes are comprehended within the meaning and range of equivalency of the following claims. The invention, therefor, is not to be restricted except as is necessitated by the prior art.

While certain novel features of this invention have been shown and described and are pointed out in the annexed claims, it will be understood that various omissions, substitutions and changes in the forms and details of the instant invention illustrated and in its operation can be made by those skilled in the art without departing from the spirit of the invention.

What is claimed is:

1. A germicidal dental floss comprising a flexible length of floss having at least on the exterior thereof a coating of a germicidal material consisting of a phenol derivative/compound and a binder of microcrystalline wax having a low melting point removably securing said material to said length of floss.

2. The floss of claim 1 comprising a coating including from 0.001 to 25 percent by weight of said germicidal material, the remainder of the coating being said binder.

3. The floss of claim 1 comprising a coating including from 25 to 75 percent by weight of germicidal material, the remainder of the coating being said binder.

4. The floss of claim 1 in which the germicidal coating includes a phenol derivative/compound in an analgesic concentration.

5. The floss of claim 1 in which the germicidal coating is 4-hexylresorcinol.

6. The floss of claim 1 in which the germicidal coating is sodium phenolate.

7. A process for making an improved dental floss comprising forming a wetting mixture of a germicidal material consisting of a phenol derivative/compound and a wax binder, applying the wetting mixture to a length of dental floss so as to form at least an outer coating thereon and solidifying said coating on said floss.

8. The process of claim 7 wherein the wetting mixture includes a solution of wax binder in a volatile solvent, which solvent is evaporated out after the application of the wetting mixture to the floss to provide a solid residue coating of said germicidal material and said wax binder on said floss.

9. The process of claim 7 in which the wetting mixture includes an aqueous emulsion of wax, the water content of which is evaporated out after the application of the wetting mixture to the floss to provide a solid residue coating of said germicidal material and said wax on said floss.

10. The process of claim 7 wherein the mixture is applied to the dental floss by pressing metering rolls saturated with the mixture against the dental floss.

11. The process of claim 7 in which the germicidal coating is 4-hexylresorcinol.

12. The process of claim 7 in which the germicidal coating is sodium phenolate.

13. The process of claim 7 wherein the mixture is applied to the dental floss by pressing felt applicators saturated with the mixture against the floss.

* * * * *